United States Patent [19]

Seeman et al.

[11] Patent Number: 5,386,020
[45] Date of Patent: Jan. 31, 1995

[54] MULTIPLY CONNECTED, THREE-DIMENSIONAL NUCLEIC ACID STRUCTURES

[75] Inventors: Nadrian C. Seeman, New York, N.Y.; Junghuei Chen, Berkeley, Calif.; Neville R. Kallenbach, New York, N.Y.

[73] Assignee: New York University, New York, N.Y.

[21] Appl. No.: 639,684

[22] Filed: Jan. 10, 1991

[51] Int. Cl.⁶ .................... C07H 21/02; C07H 21/04
[52] U.S. Cl. .................................. 536/23.1; 536/25.3
[58] Field of Search ......................... 536/25.3, 23.1

[56] References Cited

PUBLICATIONS

Ma et al., *Nucleic Acids Res.*, 14(24), 9745–9752 (1986).
Chen et al., *J. Am. Chem. Soc.* 111(16), 6402–6407 (1989).
Petrillo et al., *Biopolymers* 27, 1337–1352 (1988).

*Primary Examiner*—Margaret Parr
*Assistant Examiner*—Kenneth R. Horlick
*Attorney, Agent, or Firm*—Curtis, Morris & Safford

[57] ABSTRACT

The invention discloses an n-connected closed covalent three-dimensional structure of oligonucleotides, n being at least 3, and methods for making and using same.

14 Claims, 3 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

CGCAATCCTG AGCACG    16

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

CGTGCTCACC GAATGC    16

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear (x i) SEQUENCE DESCRIPTION: SEQ ID NO:3:

GCATTCGGAC TATGGC  16

(2) INFORMATION FOR SEQ ID NO:4:

(i) SEQUENCE CHARACTERISTICS:
(A) LENGTH: 16 base pairs
(B) TYPE: nucleic acid
(C) STRANDEDNESS: single
(D) TOPOLOGY: linear (x i) SEQUENCE DESCRIPTION: SEQ ID NO:4:

GCCATAGTGG ATTGCG  16

MULTIPLY CONNECTED, THREE-DIMENSIONAL NUCLEIC ACID STRUCTURES

This invention was made with Government support and the Government has certain rights in the invention.

FIELD OF THE INVENTION

This invention relates to a closed covalent three-dimensional structure of oligonucleotides of nanometer dimensions, and to methods of making and using the same.

Several publications are referenced in this application by arabic numerals within parenthesis. Full citation of these references is found at the end of the specification immediately preceding the claims. These references describe the state-of-the-art to which this invention pertains.

BACKGROUND OF THE INVENTION

One of the major goals of both biotechnology and nanotechnology (1,2) is the assembly of novel biomaterials that can be used for analytical, industrial or therapeutic purposes. A particular aim is to construct individual objects and devices on the nanometer scale, utilizing the informational macromolecules, e.g. polypeptides and polynucleotides, of biological systems.

Nature provides many examples of elegant polypeptide or polynucleotide constructs on a nanometer scale. For example, the type of subcellular organelle known as a ribosome is a sophisticated machine constructed of polynucleotides and polypeptides. As is well known to the art, a ribosome functions in a machine-like manner in order to "read" the genetic sequence coded by a messenger ribonucleic acid (RNA) strand and to generate the corresponding polypeptide. The ability to construct functional artificial components on a nanometer scale from polypeptides and/or nucleic acids would provide the capability of creating artificial tools and reagents able to mimic the function of natural subcellular organelles and to perform other useful functions, not necessarily present in the natural state, for diagnostic, therapeutic or industrial purposes. For example, such a construct would provide a useful 3-dimensional scaffolding upon which enzymatic or antibody binding domains may be linked to provide high density multivalent processing sites to link to and solubilize otherwise insoluble enzymes, or to entrap, protect and deliver a variety of molecular species, and the like.

Polypeptides play a variety of prominent functional roles in living cells, including enzymatic, regulatory and structural activities; hence, substantial effort has gone into the engineering of polypeptides (e.g., 3-5). However, less attention has been paid to the structural possibilities of nucleic acids. The stable form of naturally-occurring DNA is a linear double helical molecule (6), with limited potential for the construction of complex objects.

During the past several years, a number of investigations of the physical properties of deoxyribonucleic acid (DNA) branched junctions (10, 19-29), as well as their susceptibility to resolving enzymes (26, 30-32) have been reported. These studies have been stimulated by the role of branched DNA molecules as intermediates in the process of genetic recombination (33). In addition, the possibility of using branched DNA molecules to construct nanometer scale (also referred to herein as "nanoscale") objects has been explored. In prior work a series of macrocycles (cyclic trimers, tetramers, etc.) was formed by oligomerizing 3-arm junctions (34) or 4-arm junctions (35) containing a pair of complementary cohesive ends. The presence of numerous closed products from those ligations indicates a large degree of flexibility in the angles between arms (over long ligation times), regardless of how well-defined the structure of an individual junction may appear to be (27-29).

Each of these previous studies has produced a closed object that may be described as 2-connected (37). Although sharp kinks are introduced into the constructs by the presence of the junctions, the closed figures formed are essentially cyclic flexed variations on a linear theme. In addition, the earlier constructions are not inherently 3-dimensional molecules, although they may happen to be non-planar. Thus, it can be readily appreciated that provisions of a 3-connected or closed covalent three dimensional structure of oligonucleotides, and of methods of making and using such structures, would be a highly desirable advance over the current state of technology.

OBJECTS OF THE INVENTION

It is a general object of the invention to provide a closed covalent three-dimensional structure of oligonucleotides.

It is another object of the invention to provide a three-dimensional structure of oligonucleotides comprising at least four immobile oligonucleotide branched junctions covalently bonded in a closed covalent three-dimensional structure.

It is a further object of the invention to provide a three-dimensional structure of oligonucleotides comprising eight immobile oligonucleotide branched junctions covalently bonded in a closed structure.

It is yet another object of the invention to provide a closed covalent structure of oligonucleotides comprising a first immobile or partially-mobile oligonucleotide branched junction covalently bonded in a closed structure to at least three additional immobile or partially-mobile oligonucleotide branched junctions which define a plane remote from the first oligonucleotide branched junction.

It is a still further object of the invention to provide a composition of matter comprising a closed covalent three-dimensional structure of oligonucleotides covalently linked to at least one polypeptide.

It is another object of the invention to provide methods for preparing a closed covalent three dimensional structure of oligonucleotides by hybridizing and ligating at least six oligonucleotide strands to form a three dimensional object.

It is another object of the invention to provide a method for preparing a closed covalent three dimensional structure of oligonucleotides comprising hybridizing and ligating at least four immobile oligonucleotide branched junctions each having at least three arms, each arm having at least one designated complementary sequence complementary to an arm of at least one other of the junctions and each junction being hybridized and ligated to an arm of at least three other junctions.

It is yet another object of the invention to provide a method of enhancing the rate of catalysis of a multi-step chemical reaction comprising contacting the reactants with a closed covalent three dimensional structure of oligonucleotides having at least two different polypeptide catalysts for the reaction attached to the structure.

It is a still further object of the invention to provide a method of enhancing the solubility of an insoluble compound comprising attaching the compound to a closed covalent three-dimensional structure to form a complex of the structure and the compound.

These and other objects, features and advantages of the invention will become more readily apparent from the ensuing description, and the novel features will be particularly pointed out in the appended claims.

SUMMARY OF THE INVENTION

The advent of stable immobile polynucleotide branched junctions (7–10) makes DNA an excellent candidate for building framework molecules to which polypeptides or other functional molecules can be attached and thereby juxtaposed (11–13). DNA is readily synthesized (14), including short stretches of single-stranded 'sticky' ends (16). Short stretches (less than 3 turns) are fairly stiff, roughly linear building blocks (15). The addition of single-stranded 'sticky' ends (16) to branched DNA molecules converts them into macromolecular valence clusters. The specificity of sticky ends permits the construction of stick figures (7–9, 17, 18). The edges of these stick figures are double helical DNA, while the vertices correspond to the branch points of the junctions.

One of the most appealing aspects of branched DNA molecules is the presence of multiple double helical arms flanking the branch points; this feature means that these branch points can be treated as geometrical vertices, affording the possibility of forming n-connected objects and lattices ($n \geq 3$) made from DNA.

Thus, in one aspect, the present invention relates to a closed covalent three-dimensional structure of oligonucleotides. In another aspect, the invention relates to a three-dimensional structure of oligonucleotides having at least four immobile oligonucleotide branched junctions covalently bonded in a closed structure.

In a further aspect, the invention relates to a three-dimensional structure of oligonucleotides having eight immobile oligonucleotide branched junctions covalently bonded in a closed structure.

In yet a further aspect, the invention relates to a closed covalent structure of oligonucleotides formed from a first immobile oligonucleotide branched junction which is covalently bonded in a closed structure to at least three additional such branched junctions which define a plane remote from the first oligonucleotide branched junction.

In a further aspect of the invention there is provided a closed covalent structure of oligonucleotides comprising a first partially-mobile oligonucleotide branched junction covalently bonded in a closed structure to at least three additional partially-mobile oligonucleotide branched junctions which define a plane remote from the first oligonucleotide branched junction.

In a still further aspect, the invention provides a composition of matter which is a closed covalent three-dimensional structure of oligonucleotides covalently linked to at least one polypeptide.

In another embodiment, the invention provides a method for preparing a closed covalent three-dimensional structure of oligonucleotides by hybridizing and ligating at least four immobile oligonucleotide branched junctions, each junction having at least three arms, each arm having a least one designated complementary sequence complementary to an arm of one other of the junctions, and each junction being hybridized and ligated to at least three other junctions.

In still another embodiment, the invention provides a method for preparing a closed covalent three-dimensional structure of oligonucleotides by hybridizing and ligating at least eight immobile oligonucleotide branched junctions, each junction having at least three arms and each arm having at least one designated complementary sequence complementary to an arm of at least one other of the junctions, and each junction being hybridized and ligated to at least three other junctions.

In a further embodiment, the invention provides a method for preparing an n-connected closed covalent three-dimensional structure of oligonucleotides. The number n is designated the number of arms at each junction comprising the object and n is an integer in the range of from 3 to 12. More preferably, the number n is an integer in the range of 3 to 8. Even more preferably, the number n is an integer in the range of 3 to 6, and most preferably, the number n is 3. The method comprises the steps of preparing at least two closed 3-connected oligonucleotide objects, each object having at least three arms having sticky ends each complementary to a sticky end of at least one of the arms on the other object; and hybridizing and ligating each arm to its designated complement.

In another aspect, the invention is directed to a method for preparing a 3-connected closed covalent three-dimensional structure of oligonucleotides. The method comprises the steps of preparing first and second oligonucleotide quadrilaterals, each quadrilateral comprising four immobile oligonucleotide branched junctions. Each junction has at least three arms at each corner. At least one of the arms on the first quadrilateral has sticky ends is complementary to a sticky end of a corresponding arm on the second quadrilateral. Each of the arms is caused to hybridize and ligate with its designated complementary arm to form a 3-connected cube-like object.

In still another embodiment, the invention is directed to a method for preparing a 3-connected closed covalent three-dimensional structure of oligonucleotides. The method comprises the steps of preparing first and second oligonucleotide quadrilaterals, each quadrilateral comprising four immobile oligonucleotide branched junctions. Each junction has at least three arms at each corner. At least one arm on the first quadrilateral having a sticky end complementary to a sticky end of a corresponding arm on the second quadrilateral. Each of two arms on adjacent corners of the first quadrilateral is hybridized and ligated to its complement on adjacent corners of the second quadrilateral. This forms a 3-connected belt comprising three covalently bonded quadrilaterals. The 3-connected belt is separated, and the complementary arms on opposite ends of the belt are ligated to form a 3-connected cube-like object.

In yet another aspect, the invention is directed to a method for preparing a 3-connected closed covalent three-dimensional structure of oligonucleotides. The method comprises the steps of preparing first and second oligonucleotide quadrilaterals. Each quadrilateral comprises four immobile oligonucleotide branched junctions. Each junction has three arms at each corner and at least one of the arms on the first quadrilateral having a sticky end complementary to a sticky end of a corresponding arm of the second quadrilateral. Each of two arms on adjacent corners of the first quadrilateral is hybridized and ligated to its complement on adjacent corners of the second quadrilateral. This forms a 3-connected belt comprising three covalently bonded quadrilaterals. The 3-connected belt is separated, and the designated complementary arms on opposite sides of the belt are ligated to form a 3-connected cube-like object.

The invention is also directed to a method for preparing a 3-connected, closed covalent three-dimensional structure of oligonucleotides. The method comprises preparing first and second quadrilaterals by the steps of: self-ligating strand 1 to form a first cycle, and self-ligating strand 6 (SEQ ID NO: 6) to form a second cycle. Hybridizing strands 2–5 to the first cycle and hybridizing strands 7–10 to the second cycle to form first and second quadrilaterals. Each quadrilateral comprises four immobile branched junctions, each junction having three arms. Further, each of the arms has a sticky end complementary to a corresponding sticky end of an arm on the other quadrilateral. Each of the sticky ends on two arms on adjacent corners of the first quadrilateral is hybridized and ligated to its complementary sticky ends on adjacent corners of the second quadrilateral. The quadrilaterals are hybridized and ligated to each other, forming a 3-connected belt consisting of three covalently bonded quadrilaterals having two arms bearing sticky ends located at each of the opposite ends of the belt together with a mixture of other products. The 3-connected belt is denatured during electrophoresis of the mixture on a denaturing gel to obtain a separated band which is substantially a linear tricyclic topologically bonded core of the belt, and then the band comprising the tricyclic topologically bonded core is reconstituted by combination with strands 2, 3, 4, 7, 9 and 10 to form a doubly nicked, but otherwise reconstituted version of the original belt. The complementary sticky ends on the arms on opposite sides of the belt are then ligated to form a 3-connected three-dimensional cube-like object. The 3-connected three-dimensional cube-like object is then separated.

The invention further concerns methods for enhancing the rate of catalysis of a multi-step chemical reaction. This method comprises the steps of forming a closed covalent three dimensional structure and attaching at least two different polypeptide catalysts to that structure, and then running the reaction.

In still another embodiment, the invention is directed to a method of enhancing the aqueous solubility of an insoluble compound comprising the steps of forming an n-connected, closed covalent three dimensional structure where n≧3. At least one molecule of the insoluble compound is linked to the structure to form a new composition of the structure and the compound. The composition is then dissolved in aqueous solution.

BRIEF DESCRIPTION OF THE DRAWINGS

The following detailed description, given by way of example but not intended to limit the invention solely to the specific embodiments discussed, may best be understood in conjunction with the accompanying drawings, in which.

DETAILED DESCRIPTION OF THE INVENTION

The basic premise underlying the construction of a closed covalent three-dimensional structure of oligonucleotides is that DNA will form continuous perfectly-paired double helical segments in preference to other arrangements. The fact that double helical DNA which has been designed to have "sticky" ends is able to undergo hybridization only with a unique complementary sequence permits the construction of nanometer scale DNA objects by hybridization. Thus, one must design oligonucleotide subcomponents having sequences carefully selected to hybridize in a unique fashion only to the desired complementary hybridization site.

Definitions

In order to more clearly understand the invention, certain terms are defined as follows.

A nucleotide is one of four bases: adenine, cytosine, guanine, and thymine (DNA) or uracil (RNA), plus a sugar, plus a phosphate. An oligonucleotide is a sequence formed of at least two nucleotides. A polynucleotide is a long oligonucleotide. While the term "oligonucleotide" is generally used in the art to denote smaller nucleic acid chains, and "polynucleotide" is generally used in the art to denote larger nucleic acid chains, the use of one or the other term herein is not a limitation or description of size unless expressly stated to be. The use of the term nucleic acid, polynucleotide or oligonucleotide herein refers to DNA, RNA, any combination of DNA and RNA, any combination of DNA and/or RNA and/or any other base or derivative of any base which is utilizable for the present invention.

The complement to an oligonucleotide sequence is well known to be a sequence comprising those bases which will pair by Watson-Crick hybridization with the first sequence. Thus, the complement to the deoxyribonucleic acid (DNA) sequence 5' ATGC 3' is well known to be 5' GCAT 3'. The sequences have been prepared by design (using the sequence symmetry minimization procedure discussed in Design section below) so as not to hybridize with any other sequence within the oligonucleotides of the planned construct.

A sticky end (also known to the art as a cohesive end) is a single stranded portion of a first oligonucleotide designed to be complementary to a corresponding portion of another such oligonucleotide. The sticky ends are attached to arms. An arm is a double helical segment of nucleic acid that flanks a junction.

A complementary arm contains a sticky end complementary to a sticky end on another arm.

A branched function is the point from which two or more arms radiate. A branch angle is the angle between two arms. There are no known limits on the angle. A mobile branched junction is one which undergoes branch point migration. This means that the position of the junction moves with respect to the polynucleotides forming the junction e.g. a Holliday recombination intermediate. An immobile branched junction is one which is designed so that only the sequences forming the junction are able to hybridize, thus all other positions for the junction are precluded. An example of an immobile junction is the cruciform junction of FIG. 1. A partially mobile branched junction is one which is designed so that some limited migration is possible due to the availability of one or more alternative hybridization sites between the oligonucleotides forming the junction. A junction with two migratory isomers (one alternative state) is a monomobile junction (24).

Connectedness defines the number of arms forming a junction or junctions making up an object. Thus, a 3-arm junction is 3-connected, and the vertices formed by triangles tiling a floor are 6-connected. An object may be 3-connected and approximately planar, such as the belt structure which is an intermediate in the construction of the cube-like object. While all real objects are in actuality three-dimensional, including so-called linear or planar DNA molecules, it is the combination of n-connected ($n \geq 3$) and three-dimensional geometrical structure which forms a novel aspect of the present invention. The number n is designated the number of arms at each junction comprising the object and n is an integer in the range of from 3 to 12. More preferably, the number n is an integer in the range of 3 to 8. Even more preferably, the number n is an integer in the range of 3 to 6, and most preferably, the number n is 3.

The term separation when referred to in the context of the preparation of the compositions of the invention or the methods of using the invention generally refers to purification of an intermediate or a final product. The term separation when referred to in the context of the preparation of certain intermediates in the preparation of the cube-like object also encompasses the process of purification of a denatured component (e.g. of the belt), on a denaturing gel, which denatured component must then be reconstituted to form a substantially pure belt that is used to make the cube.

When a reaction proceeds in two steps, and enzyme A catalyzes step 1, and enzyme B catalyzes step 2, then the reaction is described herein as having two catalytically distinguishable reaction steps.

Design of Complementary Sequences

Sequence Symmetry Minimization

The design of the oligonucleotides of the present invention requires that the sequences of each DNA strand be sufficiently unique so that undesired hybridization is avoided and desirable hybridization is optimized. Thus, the sequences are selected with the goal of minimizing sequence similarities between segments of molecules. This serves to decrease the chances of undesired associations between segments and improve control over secondary structure. This process is known as sequence symmetry minimization.

The sequence design process assigns sequences that assemble into otherwise-unfavorable branch points in DNA by making the maximization of Watson-Crick base pairing contingent upon their formation. A systematic procedure for selecting the sequences of these 'branched junctions' is known to the art (8, 9), and may be used to aid in the design of the oligonucleotide sequences for constructing a closed covalent structure of oligonucleotides.

Although it is very difficult to predict the structure of a molecule of arbitrary sequence (52, 53), it is possible to rationally design molecules having sequences enabling the formation of a particular secondary structure (e.g., 10, 13, 19, 54). The basic premise underlying the procedure is that DNA will form continuous perfectly-paired double helical segments in preference to other arrangements.

Given enough perfect pairs, one ought to be able to form oligonucleotide strands able to assume secondary structures that would not otherwise form spontaneously. Ideally, one would prefer to have a 'vocabulary' of many different sets of complementary bases from which to draw (45), in order to form unique, yet intricate, structures. However, there are available conveniently only the two hydrogen bonding schemes defined by the classical base pairs, A—T and G—C. Therefore, longer contiguous segments, i.e., trimeric, tetrameric, pentameric or hexameric sequences, are treated as the unique components from which we may select sequences. The set of unique 'vocabulary elements' is increased to 64 (trimers), 256 (tetramers), 1024 (pentamers) or 4096 (hexamers), depending upon the length selected. These elements were termed 'critons' in earlier work (8).

The critical feature of designing molecules to assume given structure is to make it as difficult as possible for them to adopt an alternative structure.

A general requirement of the procedure for selecting the sequences of the oligonucleotide components is that all sequences complementary to a region that cannot be perfectly complemented are treated as having already been used; further use would increase sequence-symmetry.

Figure 1:
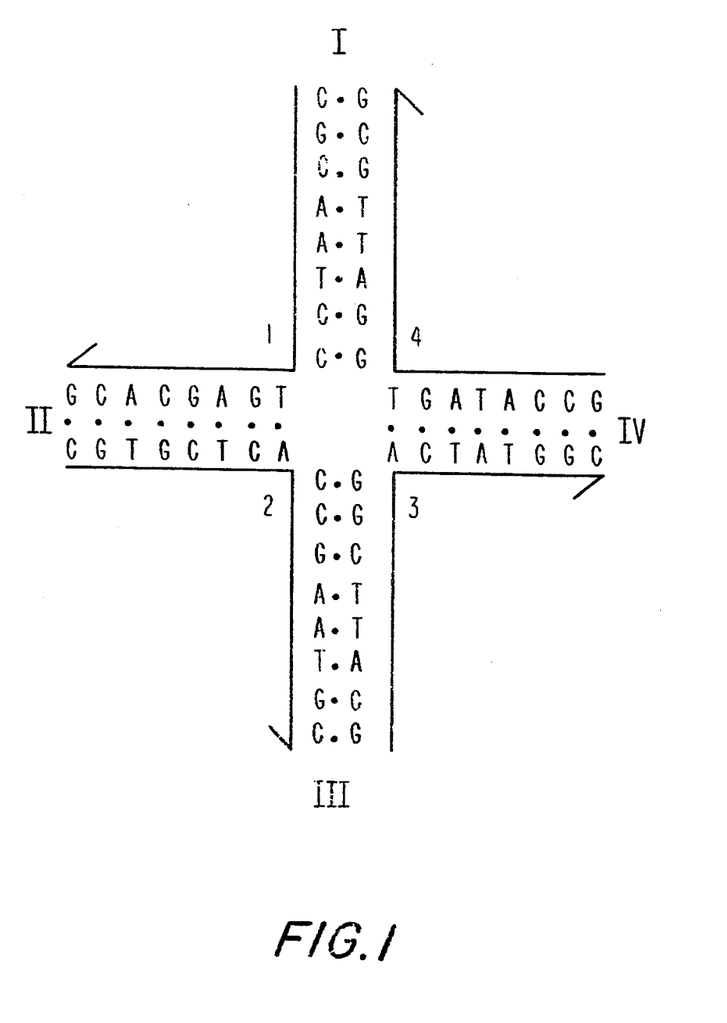
FIG. 1 is a schematic representation of a cruciform (4-arm) immobile junction, which comprises the following four sequences CGCAATCCTGAGCACG (SEQ. ID NO:1), CGTGCTCACCGAATGC (SEQ. ID NO:2), GCATTCGGACTATGGC (SEQ ID NO:3) and GCCATAGTGGATTGCG (SEQ ID NO:4).

For example, the complex shown in FIG. 1, the well-characterized junction J1 (21-23, 25, 46-47), contains four hexadecamer strands as (numbered in figure) designed by means of this procedure. The double helical arms are indicated by Roman numerals. Each hexadecamer strand consists of 13 overlapping tetramers. Thus, a hexadecamer can be regarded as a set of 14 overlapping trimers, 13 overlapping tetramers, 12 overlapping pentamers or 11 overlapping hexamers. The sequence of this junction was designed using tetrameric vocabulary elements. G—C content is intentionally high (19/32 nucleotide pairs). Each end contains two G—C pairs. No more than two G's in a row are permitted, in order to prevent G—G pairing. Note the lack of twofold symmetry in the base pairs flanking the branch point. Each of the 52 tetramer elements in the four-stranded complex is unique. Of course, if a limited amount of branch migration is desired, this may be programmed into the sequence (8, 24).

Thus, sequence-symmetry has been minimized here so that no tetrameric vocabulary element is repeated at all. To a first-order approximation, this means that competition with the designated structure comes from Watson-Crick pairing segments of length 3 or fewer (second-order analysis is discussed below). The reason for using tetramers as the vocabulary elements to design the junction is that it is too difficult (perhaps impossible) to select the 56 required unique trimers from the 64 that are available. Were it possible to use trimers, the only competitive Watson-Crick structures would be two nucleotides long.

Gel electrophoresis experiments on J1 (FIG. 1)(10) and other junctions (19, 24, 27, 34, 54), conducted under native conditions, have borne out the validity of this approach. The strands have been shown to associate in the designated fashion, and the two sets of opposite strands (which are not designed to pair) have the same electrophoretic mobilities whether their components are run separately or mixed together. Although the assumption that electrophoretic behavior is a perfect mirror of molecular association in solution must be viewed with caution, these results strongly support the effectiveness of designing secondary structure in this fashion.

The earlier approach to the construction of branched nucleic acids centered on the construction of an individual junction. In the new procedure, double helical arms are defined, and then their linking together in a particular fashion is specified. One end of an arm can terminate at a branched junction, while the other end may be linked to another arm. In this fashion, many branched junctions can be defined, and they, in turn, can be linked to form stick-polyhedra or other network components. Once the connectivity of the arms is established, the symmetry-minimization technique can be applied to the entire construct or to some large portion of it.

Computer Assisted Sequence-Symmetry Minimization

The assignment of sequence can be done with computer assistance in two different SEQUIN modes, manual or semi-automatic. In the manual mode, the designer assigns sequences one nucleotide at a time. As the user assigns the sequence of a given arm, 5' to 3' information is presented on the previous usage of the vocabulary elements (i.e., the tetramer, pentamer or hexamer ending in G, A, T or C) that constitute the choice, as well as the self-complementarity of any elements selected. For example, if one is monitoring elements of length 4, and is setting the 5th nucleotide of an arm whose first 4 are CATC, the previous usage of ATCG, ATCA, ATCT and ATCC will be displayed. If an element is repeated for some reason, the program will note this, but it will not object. This approach is in sharp contrast to the earlier procedure, which requires 100% stringency, with any multiple use of a specified-length vocabulary element leading to rejection of the sequence. Experience has shown that this level of stringency is unnecessary (13, 24, 34), and the current procedure is therefore more flexible. This relaxation is also warranted because errors in judgment are relatively inexpensive in time and materials. In addition to linear sequence symmetry, it is useful for the designer to be aware of twofold symmetry about the branch point, which permits branch migratory isomerization; this information is also made available.

The semi-automatic mode constitutes a scan of possible sequences to fill in a region, in line with a set of specified criteria. If desired, these criteria permit complete stringency for a given set of elements, for example, no repeats of pentamers. Alternatively, they may be relaxed to allow particular violations of minimum-symmetry rules, requiring no repeats in any new elements selected, but permitting repeats in those already present. Experience with this procedure suggests that this mode is most effective. The usual design situation involves a well-defined set of often-symmetric sequences that must go into the structure—restriction sites, B—Z-sites, $T_n$-loops, or junction-flanking sequences—that will violate the usual stringent criteria. It is desirable to design the remaining sequences in such a way that the rest of the molecule will assemble into a particular architecture. The SEQUIN program presents the user serially with all the sequences that fulfill the specified criteria for a short segment, and any of these sequences may be assigned to the segment.

The more relaxed approach presented here facilitates the elimination of exhaustive scans of sequence-space seeking the 'best' sequence. If the user knows the overall characteristics of a sequence in a given region, e.g., percent GC, eschewal of GGG strings (56–58), or avoidance of polypurine tracts (59–61), these features can be incorporated into manual or semi-automatic sequence assignment; sequences containing unwanted features may be rejected in both assignments modes.

Since pairing interactions occur within double helical arms, it seems most logical to assign sequences in the context of defining an arm. Nevertheless, the individual covalent molecules that are synthesized, and which associate with each other to form the complex, are single-strands that participate in two or more arms. From the linkages assigned by the designer, the program determines the sequences of the strands, and performs a number of diagnostic tests upon them, such as searching for inverted repeats that lead to self-pairing.

In addition, it is useful to test each strand against every other strand to discover unanticipated near-complementarities. These can arise from the failure of the first-order approximation to sequence-symmetry minimization mentioned above: For example, the first-order approximation, with tetramer elements, would be insensitive to the virtual identity between ACCAATG and ACCGATG because they do not share any tetramer elements. G—T or G—U pairing can be included as valid pairs in this form of analysis. Analysis is also facilitated with simple energy calculations using dimer energies for either DNA (62) or RNA (63).

Once the connectivity of a molecule is defined, and a satisfactory sequence is worked out, it is convenient to use it as the basis for further work. Therefore, a SEQUIN file-structure allows the storage and retrieval of molecules: Multiple molecules may be retrieved, and aggregates can be assembled and stored. Files are in card-image format so that modifications can be made through the system text editor.

SEQUIN Functions

The key function of the program SEQUIN is tabulation of vocabulary element usage. Thus, during the assignment of sequence, the program is automatically or manually instructed to calculate element usage for all of the allowable vocabulary element lengths (trimers to hexamers). As described above, usage includes not only explicit assignment to a given strand or complement, but also implicit assignment as the unwanted complement of a sequence that spans a branch point or forms a loop. The table containing this information is used both analytically and for purposes of further sequence assignment. The main analytical value of the table is to indicate which elements have been used repetitively; for example, adding two structures together can result in sequence repetition that one wishes to know about. Both the manual and semi-automatic sequence assignment procedures rely upon this table for keeping element repetition at a minimum. The manual assignment procedure can also keep track of nucleotides that flank junctions, thereby allowing the user to eliminate sequences with twofold symmetries that permit branch migration.

The following are the steps one goes through in using the SEQUIN program: [1] Definition of connectivity: arms of particular lengths are defined, and junction branches, single-stranded loops, and double-stranded linkages between arms are specified. [2] Fixed sequences are inserted: restriction sites, Z-loci, oligo-T loops, polypeptide binding sites, and other regions that may contain sequence-symmetry are included if desired. [3] Sequence assignment is performed using the manual or (more likely) the semi-automatic procedure. [4] The sequence is analyzed by means of the analytical machinery of the SEQUIN program. [5] When satisfactory, the structure and sequence are stored, and the sequences of the component strands are output for synthesis. [6] The stored structure may be used as the basis for related structures.

Geometry

Geometry of a unit Structure

A single unit of a closed covalent three-dimensional structure of oligonucleotides could assume any of a number of geometries. Of course, the skilled artisan can appreciate that the helical duplex DNA does not behave as an ideal rigid mechanical rod, and the angles are not fixed at 90° thus all geometrical shape names are approximations. The term "square" encompasses the whole family of planar quadrilaterals, and also encompasses such quadrilaterals which may not be perfectly coplanar due to the conformational variations of the duplex polynucleotides from which such shapes are formed. Similarly, a "cube" may be in actuality cube-like, i.e. in a generally cubic shape. A cube may also refer to any of the permutations of eight-cornered figures known to the skilled artisan to have edges of approximately equal length, but not necessarily having straight edges or equal angles at the corners. Analogous definitions allowing for the imperfect rigidity of polynucleotides and flexible angle formation at junctions (corners) apply to the terminology of all other geometrical 3-connected, three-dimensional shapes referred to herein.

Structures which could desirably be assembled include a pyramid-like structure, a cube-like structure, and higher numbered polyhedra including a truncated octahedron. As one example of the constructs which may be achieved by the present invention, a cube-like closed covalent three dimensional structure of oligonucleotides is exemplified. cl Geometry of a Lattice or Array of Unit Structures The unit structures described above are linked by Watson-Crick or covalent bonding to form a lattice or array. The geometry may be repeating units of pyramidal, cube-like or higher polyhedra, for example a truncated octahedron. The units may be linked in linear fashion, a planar fashion, e.g., to form a sheet of unit structures, or a super polyhedron of n by m by 1 unit structures where 1, m and n are integer numbers of units greater than 1. Other, more elaborate geometric structures may be constructed by applying the same principles of connectivity.

Assembly

Assembly of a Unit Cube-Like Structure

There are several different ways that a cube-like molecule can be designed and then assembled. A major variable is the amount of flexibility assumed for the junction. If one were to assume low flexibility, several options would be available (17,18), using 4-arm junctions or 6-arm junctions (11,38). Advantageously, 3-arm junctions are used for creating a cube-like structure which is not attached to another such structure.

Two options present themselves: [1] 3-arm junctions separated by an integral number of turns and [2] 3-arm junctions separated by $(2n+1)/2$ turns (n integral). The second option would form the same array of helix axes as in [1], but would be composed of 4 cyclic single strands, each participating in six helical segments, rather than 6 strands, each participating in four helical segments. The first option was adopted, because the second seems to offer fewer tests of the construction. This design cleanly isolates each face as a separate cyclic molecule, rather than isolating the hexagonal projections of the cube.

Twenty nucleotide pairs were used for each edge. Although the canonical number of nucleotide pairs in two turns of DNA is currently believed to be about 21 for linear DNA (39, 40), it has been empirically determined that 20 pairs work better with this scheme.

Figure 2:
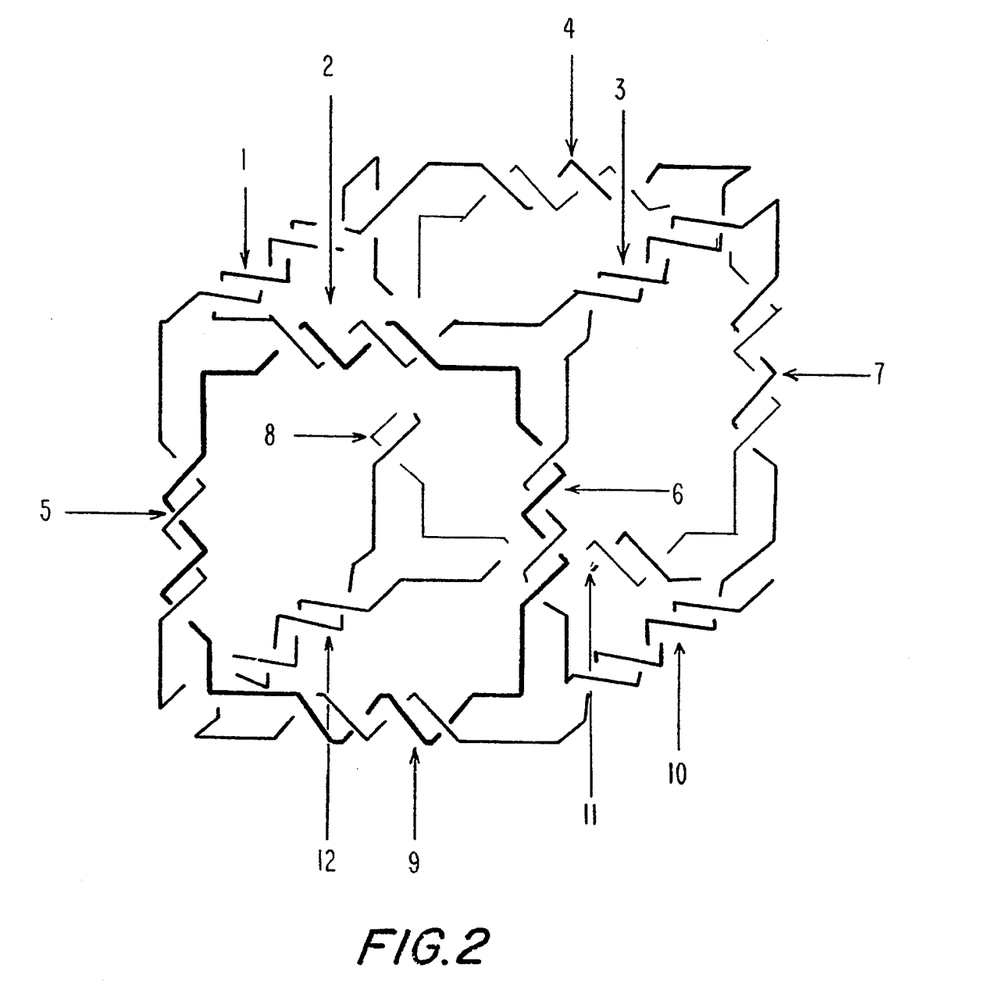
FIG. 2 is a schematic representation of a preferred embodiment of this invention for a closed covalent three-dimension structure of polynucleotides having a cube-like geometry. The numbers indicate the different restriction sites on the twelve edges of the molecule.

A schematic version of the selected molecule is illustrated in FIG. 2. For simplicity, the object is shown as a cube, although there has been no characterization of the angles between the edges. The object contains 12 edges formed from double helical DNA. Each edge is numbered, and the numbers are indicated as being associated with thunderbolt-shaped arrows. These arrows indicate not only the edge numbering, but also the 12 unique restriction sites in the molecule. Edges 1–4 form the top of the object, edges 5–8 form the vertical sides of the object, and edges 9–12 form the bottom. The restriction sites are: 1—Dde I; 2—BstE II; 3—Sau96 I; 4—BstN I; 5—Rsa I; 6—BstU I; 7—Hha I; 8—Alu I; 9—Hinf I; 10—Taq I; 11—Sty I; 12—Hae III. For clarity, the double helicity of the DNA has been represented merely as parallel lines in the vicinity of the branch sites, and twisting is confined to the central portion of each edge; nevertheless, all the twisting expected in the object is shown. Since each edge contains 20 nucleotide pairs of DNA, the length of the edges is expected to be about 68 Å. From model building (43), the axis-to-axis distance across a square face appears to be about 100 Å, with a volume (in a cubic configuration) of approximately 1760 nM$^3$, when the cube is folded so that major grooves form the outsides of the corners; it is markedly smaller than when the corners are formed from minor grooves. Note that each vertex corresponds to the branch point of a 3-arm junction. Another way to regard the object is as a complex of 6 cycles, each doubly linked to its four nearest neighbors.

Figure 3:
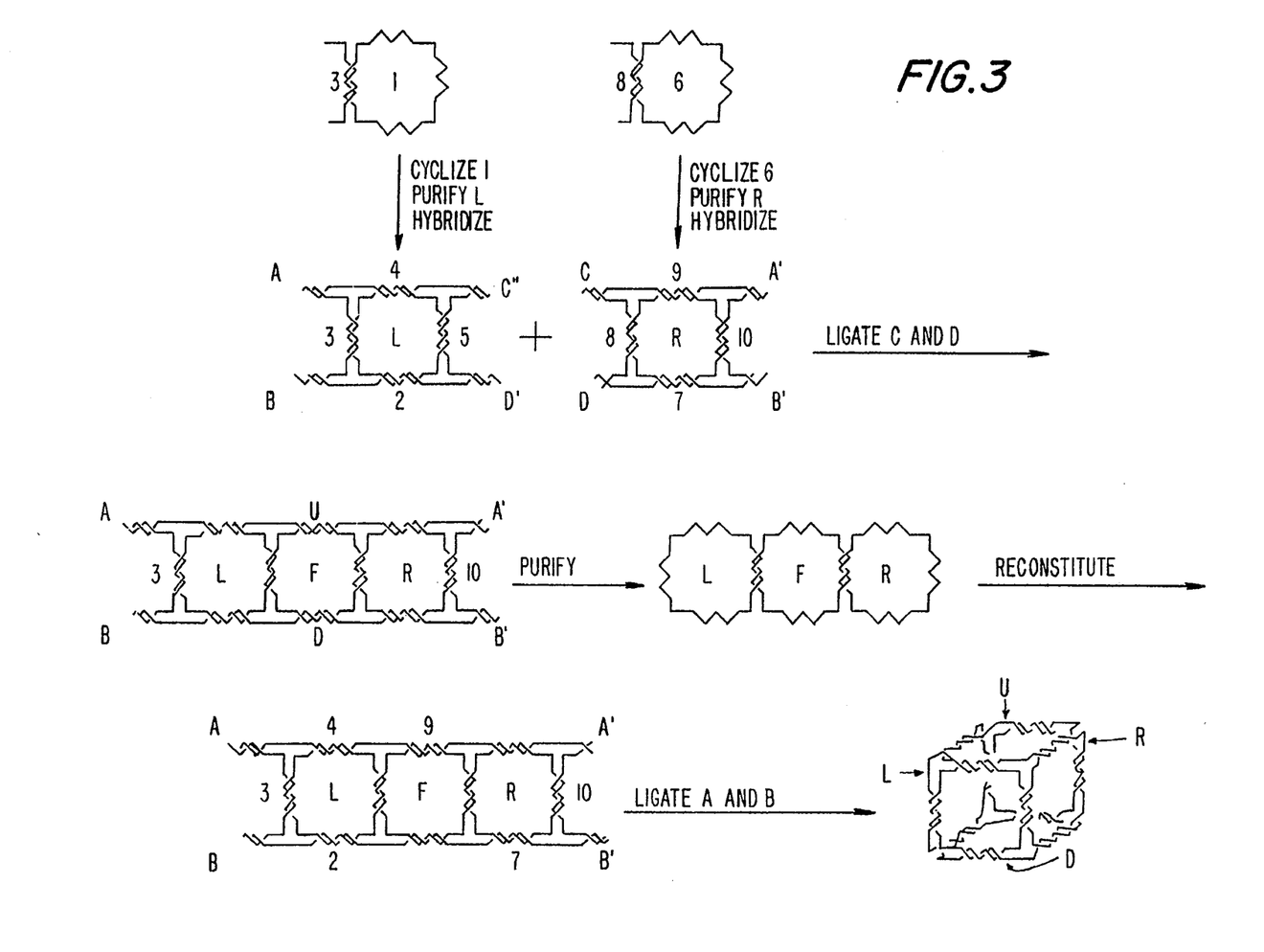
FIG. 3 represents a schematic representation of the reaction scheme by which the cube-like structure of FIG. 2 is assembled from two quadrilaterals, L and R, which are in turn ligated to form the L, F, R belt, which is purified on a denaturing gel, reconstituted and ligated to form the cube-like structure.

Alternative strategies for assembly of the unit structure include synthesizing each of the 6 final strands, then annealing and ligating them, either in one step or successively. Another alternative entails synthesis of each of the 24 strands comprising the eight 3-arm junctions that define each corner. The selected alternative, shown schematically in FIG. 3, is to synthesize ten strands corresponding to two squares, and then to ligate the free ends together.

Assembly of a Lattice of Unit Structure

The synthesis of a multi-unit lattice of unit structures is undertaken by utilizing multiple junctions of from 4 to 12 arms, thus providing the extra links (arms) needed to permit formation of one multi-unit lattice by means of Watson-Crick hybridization.

Utility

There are a large number of ways in which a closed, covalent three-dimensional DNA construction can be utilized by the skilled artisan using techniques well known to the art. By way of example, a closed, covalent three-dimensional DNA construct structure, or a lattice of multiple such structures, serves as an attachment point for multiple enzymes in order to increase the efficiency and selectivity of a multi-enzyme catalytic reaction pathway. The structure is highly soluble in aqueous solution, thus an insoluble molecule (e.g. an industrial enzyme) attached to the structure will be rendered solubilized for any number of useful purposes. The closed, covalent oligonucleotide structure or a lattice of multiple such structures can serve to trap or protect selected molecules in order to facilitate the delivery of a pharmaceutical or separate the stages of a chemical reaction.

The invention may be better understood by reference to the following examples.

EXAMPLE 1

Preparation of Starting Materials

The DNA oligonucleotides were designed by applying the principles of sequence symmetry minimization, and incorporating 12 restriction sites therein to enable analysis of the assembly intermediates and proof of the final product. The selected starting sequences are strands 1-10 (SEQ ID NO:'s 1-10).

The DNA molecules were synthesized on an Applied Biosystems 380B automatic DNA synthesizer, removed from the support and deprotected using routine phosphoramidite procedures (14). DNA molecules SEQ ID NO's 1-10 were purified from denaturing gels. Hybridized complexes were formed by mixing a stoichiometric quantity of each strand, as estimated by O.D.$_{260}$; this mixture was then heated to 90° C. for 5 minutes and slowly cooled. Errors in stoichiometry were corrected by electrophoresing the complex on a non-denaturing gel, and extracting the appropriate band from the gel. Except as noted, all gels contained 6% polyacrylamide (19:1, acrylamide: bis).

EXAMPLE 2

Assembly of the Cube

The assembly of the cube-like structure required the development of a scheme to produce useful quantities of successfully ligated products, and intermediate products of a well defined nature which could be analyzed.

In principle, only two ideal steps of those indicated in FIG. 3 are necessary for the synthesis of the cube: [1] the ligation of C and D, simultaneously with the covalent cyclization of strands 1 and 6, followed by [2] the ligation of A and B. However, the overall efficiency of the 6 ligations implicit in the first ideal step is so low, and removal of failure products is so difficult, that virtually no material could be accumulated for the second step. Consequently, the first ideal step has been broken into four separate steps A through D.

FIG. 3 illustrates the strand identification used in the text. Numbers refer to strand numbers (SEQ ID NO:s 1-10). As a new strand is formed by ligation, its identification changes from one or more numbers to a letter corresponding to its position in the final object. For example, strand 1 (SEQ ID NO: 1) is synthesized as a linear molecule, but is referred to as L, once it is cyclized. The six final strands in the object are referred to as L (left), R (right), U (up), D (down), F (front) and B (back). This scheme depicts 5 steps (separating 6 stages) in the synthesis of the 3-dimensional, 3-connected DNA object, after individual strands have been purified.

The first step involved the cyclization of the full-length strands 1 and 6 to form L and R, respectively. These two cycles were then hybridized with strands 2-5 and 7-10, respectively, to form the constituent squares shown in the second step. These squares were ligated together at the complementary sticky ends C and C' (5 base 5' overlap) and D and D' (4 base 3' overlap). This reaction formed strands U, F and D from their constituents. U and D were discarded in a purification on a denaturing gel that isolated the L-F-R triple complex. The L-F-R-2-3-4-7-9-10 complex was then reconstituted to form the L-F-R-belt of three linked quadrilaterals.

A. Closure of the Left and Right Circles

Initially, it was hoped to achieve closure of strand 1 (SEQ ID NO: 1) (to form strand L) and strand 6 (SEQ ID NO: 6) (to form strand R), in the same step in which C is linked to C' and to D'. However, it was determined that ligation is inefficient in this system. Therefore, strands 1 and 6 (SEQ ID NO:'s 1 and 6) were closed before hybridizing the shorter strands 3 and 8 (SEQ ID NO:'s 3 and 8) to them. This procedure decreases from 6 to 4 the number of strand ligations that must be done successfully in the C and D ligation step. Essentially, in the first stage synthesis, the 80-mer circles, strands 1 and 6 were phosphorylated, cyclized by ligation, and purified from denaturing gels before they were associated with the other strands that comprise their squares.

B. Hybridization to Form the L and R Quadrilaterals

The association of L with strands 2-5 (SEQ ID NO:'s 2-5) was demonstrated by gel electrophoresis; similar results were obtained with R and strands 7-10 (SEQ ID NO:'s 7-10). It was further shown that these 5th order reactions go largely to completion. In the second stage of phosphorylation, the two squares were annealed with only those phosphates on the ends corresponding to C, C', D and D'. Therefore, the squares were joined at this point, and not at the A or B sites. Extra bands were identified in the product lane corresponding to imperfect stoichiometry that were eliminated when the quadrilateral bands were cut out of the gel preceding ligation. Nevertheless, association as pentameric squares does not guarantee that all strands are double helical. For example, strand 2 (SEQ ID NO: 2) might be paired with strand 3 and strand 5 (SEQ ID NO:'s 3 and 5), but not with strand L. Susceptibility to restriction endonuclease was the assay selected to demonstrate perfect pairing, since most of the restriction sites built into the oligonucleotides making up the cube corresponded to restriction enzymes with exclusively double helical activity. In each case, this type of analysis indicated that complete hybridization was achieved in the relevant strands.

C. Ligation of the Squares

The next step was ligation of square L to square R to form the tri-cyclic belt shown at the third stage of FIG. 3. This reaction can be done in 4 different ways: ligation of C and D (as shown in FIG. 2), ligation of A and B, ligation of A and C or ligation of B and D. All four ways provided approximately equal levels of success. The choice was controlled by choosing which sticky ends are phosphorylated. The third phosphorylation, done before reconstitution, put a 5' phosphate on all unphosphorylated strands and was followed by the final ligation. Taking the ligation of C and D as an example, at 100 nM concentrations, a multitude of products was obtained, indicating that closure of the F circle occurred 10% of the time.

The desired product of the ligation was not separable from other products by electrophoresis on non-denaturing gels. The signature of successful double ligation of C and D was a 3-circle catenated intermediate (L-F-R) (tricyclic core) seen after treatment with exonuclease III. When the products of ligating cohesive ends C and D were analyzed on denaturing gels, many species were seen in addition to the 3-circle catenate. This was demonstrated by electrophoresis on a denaturing gel characterizing the exo III-resistant bands following ligation of cohesive ends C and D. Similarly, proof that the hallmark L-F-R tricyclic core was truly the expected 3-circle catenate was provided by electrophoresis. Electrophoresis also demonstrated the products obtained when 21 nucleotide pairs per edge were used, rather than 20; in which case the L-F-R band was virtually absent.

Each square was designed to contain no contiguous stretch of 6 nucleotides (7–9, 41, 42) that occurred more than once. Only 28 of 480 such sequences were duplicated in the entire cube, once the product was formed.

Proof of formation of the quadrilateral was by electrophoresis. An electrophoretic autoradiogram indicated the ligation of two quadrilaterals to form the belt structure shown in FIG. 3, following ligation of ends C and D.

Similar results were obtained with each of the four possible belts. The cube co-migrated with a standard containing 5 of the six strands in conventional denaturing gels. These two species were separable by electrophoresis on 13% denaturing polyacrylamide gels containing 80:1 acrylamide:bisacrylamide; the slower-migrating of the two bands was isolated and identified. The yield from this step was about 10%, for an overall efficiency of 1%.

D. Purification and Reconstitution of the Belt

In order to separate out pure starting material for the final ligation step, the separation was performed in two steps. Firstly, the catenated L-F-R core of the belt was purified on a denaturing gel, and secondly, the catenated core was reconstituted by adding the missing six strands. Each reconstituted strand was phosphorylated, with the appropriate strands being labeled for future analysis. To demonstrate that each of these strands was properly linked with the catenated core, restriction analysis of each of the edges containing an un-nicked double helical region was performed. In each case, the digestion went to completion, demonstrating that the reconstitution was successful for all strands, and that unlinked impurities were not created which are perhaps more flexible, and therefore more highly reactive in the closure reaction.

E. Final Closure of the Belt to Form the Cube

The cube was designed to consist of 6 linked circles, corresponding to the 6 faces of the object. These were labeled (FIG. 3) as L (left), R (right), U (up), D (down), F (front) and B (back). The final ligation was designed to form the U, B and D circles from the L-F-R belt.

The final ligations were performed to close sites A and A' (4 base 5' overlap) and B and B' (5 base 3' overlap), as well as to seal the nicks in U (4–9) and D (2–7). This series of reactions formed the entire three-dimensional, 3-connected object.

Restriction of the original L-F-R belt-core, within the isolated cube, followed by electrophoresis revealed another UBD tricyclic belt-core, indicating that all ligations had gone to completion in this isolated material. Restriction that separated what had been the top of the belt from the bottom, within the isolated cube, followed by electrophoresis revealed a single 80-mer circle; absence of 160-mer circles indicated that no detectable doubling of the belt occurred.

EXAMPLE 3

Analysis of the Cube-Like Structure

Analysis of the cube-like structure involved several different tests. Restriction of every arm individually resulted in the production of a 4-circle molecule. Restriction of the L-F and F-R edges resulted in the U-B-D triple catenane, as demonstrated by electrophoresis. Various other products were generated by double digests of opposite edges of the same square, as demonstrated by electrophoresis. Double digestion of adjacent edges of the same square resulted in cyclic-triple-catenanes, in which each circle was linked to both its neighbors, as demonstrated by electrophoresis. Determination of whether the final product corresponded to a single cycle of the belt or to multiple cycles (octagonal prism, dodecagonal prism, etc.) was established by slicing through the four parallel edges (L-F, F-R, R-B and B-L) (only three cuts are necessary), and then sizing the labeled U or D strand.

The species produced by restriction of the final 18 product were characterized by electrophoresis.

EXAMPLE 4

The Closed, Covalent Oligonucleotide Structure As Support for a Multi-enzyme System Numerous chemical reactions of commercial interest may be catalyzed by a series of different enzymes representing an artificial enzyme pathway. By attaching these enzymes to the closed, covalent oligonucleotide structure exemplified herein, such a multi-enzyme reaction will benefit from enhanced selectivity and kinetics due to decreased diffusion distances between the different enzymes, and other factors.

A. The Reaction and Enzymes

To illustrate how such a closed, covalent three-dimensional oligonucleotide structure with attached enzymes may be usefully prepared, consider the 3-enzyme reaction reported by Fraser and Rich (48) for producing 3'-amino-3'-deoxy adenosine triphosphate by catalysis from 3'-amino-3'-deoxyadenosine utilizing in a single solution: rabbit liver adenosine kinase ("RLAK"), rabbit muscle myokinase ("RMM") and pyruvate kinase ("PK"). Each step of this reaction is a catalytically distinguishable reaction step which requires a different enzyme catalyst for the reaction to run at a useful rate.

B. Linking the Enzymes to a Closed, Covalent Oligonucleotide Structure

Attaching the RLAK, RMM, and PK enzymes to the same closed, covalent oligonucleotide structure puts them in close proximity to one another. Thus, the reaction substrates and substrate intermediates are able to diffuse between each type of enzyme in less time, and the total reaction rate is increased.

The enzymes are linked to the cube-like structure of Example 2 by the method of Jablonski et al. (49). This is done by preparing one or more of the oligonucleotides used to construct the cube structure with a modified thymidine ("T") incorporated. The modified T is in the form of a phosphoramidite linker (a T with a long-chain amine attached to the 5 position). The modified T is commercially available from Glen Research, Inc. Hearndon, Va., product number 10-1039-90.

The linkers are located near the middle portions of the edges of the cube formed by the pairing of strands L and 2, 4 and 5, or R and 7, 9, and 10. At least 3 linkers, and preferably many more, are built into the oligonucleotide structure of the cube. Then, the RLAK, RMM, and PK enzymes are attached to the linker arm by the method of Jablonski et al. (49)

The linking reaction is performed in the presence of an equimolar mixture of the RLAK, RMM, and PK enzymes which will result in the random attachment of all three enzymes, on average, to each cube. The ratio of enzyme in the attachment solution may be adjusted to conform the average numbers of each type of enzyme bound to each cube to a desired kinetic ratio and performance.

Attachment of specific enzyme to specific locations on the cube is achieved by attaching each enzyme to a particular strand before hybridization.

C. Catalysis by the Enzyme - Cube Complex

The reaction is run according to the method of Fraser and Rich (48). The starting substrate, 3'-amino-3'-deoxyadenosine, is incubated with the cube-enzyme in a solution of 8 $\mu$mol ATP, 300 $\mu$mol posphoenol pyruvate, 5 $\mu$mol $MgCl_2$, 500 $\mu$mol KCl, and 1.25 ml glycerol in a reaction mixture of 12.5 ml maintained at pH 5.8 by 7 mM Tris-maleate buffer. The final concentration of 3'-amino-3'-deoxy adenosine triphosphate is determined by standard methods well known to the art. The final product may be separated by methods well known to the art (50).

The optimal concentration of cube-enzyme is determined by straightforward calibration to determine the desirable enzyme concentration in light of the substrate turnover and other kinetic reaction parameters which are well known to the art (51).

An amount of cube-enzyme wherein each cube has at least one of each of the three types of enzyme attached will catalyze the three step reaction significantly faster than would the same concentration of three enzymes in solution due to the shortened diffusion pathway between the RLAK, RMM, and PK compared to the diffusion pathway present in solution.

EXAMPLE 5

Solubilization of Insoluble Polypeptide

Due to the highly soluble nature of the 3-connected, closed, covalent oligonucleotide structure exemplified herein, any useful polypeptide which is insoluble is rendered soluble when linked to the cube by the linking methods disclosed by Example 4. Thus, otherwise useful industrial enzymes or other compounds or polypeptides which lack utility in aqueous solution due to their lack of solubility are, when linked to the cube-like structure, rendered soluble and useful in aqueous solution.

Bibliography

1. Feynman, R. P., in *Miniaturization*, ed. by M. D. Gilbert, Reinhold Publishing Corp., New York, 282-296 (1961).
2. Drexler, K. E. (1981), *Proc. Nat. Acad. Sci. (USA)* 78, 5275-5278.
3. Leatherbarrow, R. B. and Fersht, A. R. (1986), *Protein Eng.* 1, 7-16.
4. DeGrado, W. F., Wasserman, Z. R. and Lear, J. D. (1989), *Science* 243, 622-628.
5. Anthony-Cahill, S. J., Griffith, M. C., Noren, C. J., Suich, D. J. and Schultz, P. G. (1989), *Trends in Biochem. Sci.*, 14, 400-403.
6. Watson, J. D. and Crick, F. H. (1953) *Nature (London)* 171, 737-738.
7. Seeman, N. C. (1981), in *Biomolecular Stereodynamics*, ed. by R. H. Sarma, Adenine Press, New York, pp. 269-277.
8. Seeman, N. C. (1982), *J. Theor. Biol.* 99, 237-247.
9. Seeman, N. C. and Kallenbach, N. R. (1983), *Biophys. J.* 44, 201-209.
10. Kallenbach, N. R., Ma, R.-I. and Seeman, N. C. (1983), *Nature (London)* 305, 829-831.
11. Robinson, B. H. and Seeman, N. C. (1987), *Prot. Eng.* 1, 295-300.
12. Hopfield, J. J., Onuchic, J. N. and Beratan, D. N. (1988), *Science* 241, 817-820.
13. Chen, J.-H., Kallenbach, N. R. and Seeman, N. C. (1989), *J. Am. Chem. Soc.* 111, 6402-6407.
14. Caruthers, M. H. (1982), in *Chemical and Enzymatic Synthesis of Gen Fragments*, eds. Gassen, H. G. and Lang, A., (Verlag Chemie, Weinheim), pp. 71-79.
15. Hagerman, P. J. (1988), *Ann. Rev. Biophys. & Biophys. Chem* 17, 265-286.
16. Cohen, S. N., Chang, A. C. Y., Boyer, H. W. and Helling, R. B. (1973), *Proc. Nat. Acad. Sci. (USA)* 70, 3240-3244.
17. Seeman, N. C. (1985a), *J. Biomol. Str. & Dyns.* 3, 11-34.
18. Seeman, N. C. (1985b), *J. Mol. Graphics* 3, 34-39.
19. Kallenbach, N. R., Ma, R.-I., Wand, A. J., Veeneman, G. H., van Boom, J. H., and Seeman, N. C. (1983b), *J. Biomol. Str. and Dyns.* 1, 158-168.
20. Seeman, N. C. Maestre, M. F., Ma, R.-I. and Kallenbach, N. R., in *Prog. Clin. & Biol. Res.* 172A: *The Molecular Basis of Cancer*, ed. by R. Rein, Alan Liss Inc., New York, 1985, pp. 99-108.
21. Wemmer, D. E., Wand, A. J. Seeman, N. C. and Kallenbach, N. R. (1985), *Biochemistry* 24, 5745-5749.
22. Marky, L. A. Kallenbach, N. R., McDonough, K. A. Seeman, N. C. and Breslauer, K. J. (1987), *Biopolymers* 26, 1621-1634.
23. Churchill, M. E. A. Tullius, T. D., Kallenbach, N. R. and Seeman, N. C. (1988), *Proc. Nat. Acad. Sci. (USA)* 85, 4653-4656.
24. Chen, J.-H., Churchill, M. E. A., Tullius, T. D. Kallenbach, N. R. and Seeman, N. C. (1988), *Biochemistry* 27, 6032-6038.
25. Cooper, J. P. and Hagerman, P. J. (1987), *J. Mol. Biol.* 198, 711-719.
26. Duckett, D. R., Murchie, A. I. H., Diekmann, S. Von Kitzing, E. Kemper, B. and Lilley, D. M. J., *Cell* 55, 79-89 (1988).
27. Seeman, N. C., Chen, J.-H. and Kallenbach, N. R. (1989), *Electrophor.*, 10, 345-354.
28. Cooper, J. P. and Hagerman, P. J. (1989), *Proc. Nat. Acad. Sci. (USA)* 86, 7336-7340.
29. Murchie, A. I. H., Clegg, R. M., yon Kitzing, E. Duckett, D. R., Diekmann, S., and Lilley, D. M. J. (1989), *Nature* 341, 763-766.
30. Evans, D. H. and Kolodner, R. (1987), *J. Biol. Chem.* 262, 14826-14836.
31. Dickie, P. McFadden, G. and Morgan (1987), A. R., *J. Biol. Chem.* 262, 14826-14836.
32. Mueller, J. E., Kemper, B., Cunningham, R. P., Kallenbach, N. R. and Seeman, N. C. (1988), *Proc. Nat. Acad. Sci. (USA)* 85, 9441-9445.
33. Holliday, R. (1964), *Genet. Res.* 5, 282-304.
34. Ma, R.-I., Kallenbach, N. R., Sheardy, R. D., Petrillo, M. L. and Seeman, N. C. (1986), *Nucl. Acids Res.* 14, 9745-9753.

35. Petrillo, M. L., Newton, C. J. Cunningham, R. P., R.-I. Ma, Kallenbach, N. R. and Seeman, N. C. (1988), *Biopolymers* 27, 1337-1352.
36. Landegren, U., Kaiser, R., Sanders, J. and Hood, L. (1988), *Science* 241, 1077-1084.
37. Wells, A. F., *Three-dimensional Nets and Polyhedra* (1977), John Wiley & Sons, New York, pp. 3-3.
38. Mueller, J. E., Kallenbach, N. R. and Seeman, N. C. (1987), abst. 5th Conv. Disc. Biomol. Stereodyns., 127-127.
39. Wang, J. C. (1979), *Proc. Nat. Acad. Sci. (USA)* 76, 200-203.
40. Rhodes, D. and Klug, A. (1980), *Nature* 286, 573-578.
42. Seeman, N. C. (1990), *J. Biomol. Str. & Dyns.*, in press.
43. Seeman, N. C. (1988), *J. Biomol. Str. & Dyns.* 5, 997-1004.
44. Williams, R. (1979), *The Geometrical Foundation of Natural Structure*, Dover, N.Y.
45. Piccirilli, J. A., Krauch, T., Moroney, S. E. and Benner, S. A., *Nature* 343, 33-37 (1990).
46. Seeman, N. C., Maestre, M. F., Ma, R.-I and Kallenbach, N. R., in *Prog. Clin. & Biol. Res.* 172A: *The Molecular Basis of Cancer*, ed. by R. Rein, Alan Liss Inc., New York, pp. 99-108 (1985).
47. Kallenbach, N. R., Seeman, N. C. *Cmts. on Cell. and Mol. Biophys.* 4, 1-16 (1986).
48. Fraser and Rich *Proc. Nat. Acad. Sci. (USA))* 70, 2671-2675 (1973).
49. Jablonski et al. *Nucleic Acids Research* 14, 6115-6128 (1986).
50. Reference 48, ID.
51. Enzyme Kinetics A. Cornish-Bowden and C. W. Wharton. Ed. D. Rickwood, Pub. IRL Press, Oxford, Washington, D.C.
52. Jaeger, J. A., Turner, D. H. and Zuker, M., *Proc. Nat. Acad. Sci. (USA)* 86, 7706-7710 (1989).
53. Zuker, M., *Science* 244, 48-52 (1989).
54. Kimball, A., Guo, Q., Lu, M., Cunningham, R. P., Kallenbach, N. R., Seeman, N. C. and Tullius, T. D., *J. Biol. Chem.* 265, 6544-6547. (1990).
55. Seeman, N. C. and Kallenbach, N. R., in *Molecular Structure: Chemical and Biological Activity*, ed. by J. J. Stezowski, J.-L. Huang and M.-C. Shao, Oxford University Press, Oxford, pp. 189-194 (1988).
56. Williamson, J. R., Raghuraman, M. K. and Cech, T. R., *Cell* 59, 871-880 (1989).
57. Sundquist, W. I. and Klug, A., *Nature* 342, 827-829 (1989).
58. Sen, D. and Gilbert, W., *Nature* 344, 410-414 (1990).
59. Koo, H.-S., Wu, H.-M., and Crothers, D. M., *Nature* 320, 501-506 (1986).
60. Lyamichev, V. I., Mirkin, S. M. and Frank-Kamenestskii, M. D., *J. Biomol. Str. & Dyns.* 3, 327-338 (1985).
61. Htun, H. and Dahleberg, J. E. *Science* 241, 1791-1796 (1988).
62. Breslauer, K. J., Frank, R., Bloecker, H., and Marky, L. A., *Proc. Nat. Acad. Sci. (USA)* 83, 3746-3750 (1986).
63. Freier, S. M., Kierzek, R., Jaeger, J. A., Sugimoto, N., Caruthers, M. H., Nellson, T., and Turner, D. H., *Proc. Nat. Acad. Sci. (USA)* 83, 9373-9377 (1986).

---

What we claim is:

1. A closed three-dimensional oligonucleotide structure comprising y junctions, each junction comprising n double-stranded oligonucleotide arms, wherein: y=8 and n=3, said arms form 12 edges, and every nucleotide residue in said structure is covalently bonded at its 5' and 3' ends to another nucleotide residue.

2. The structure of claim 1 wherein the junctions are at least four immobile oligonucleotide junctions.

3. The structure of claim 1 wherein the junctions are eight immobile oligonucleotide junctions.

4. The structure of claim 1 wherein the oligonucleotide arms are DNA.

5. The structure of claim 1 wherein the oligonucleotide arms are RNA.

6. The structure of claim 1 wherein the structure is in the shape of a cube.

7. The structure of claim 1 wherein the junctions are at least four partially-mobile oligonucleotide junctions.

8. A method for preparing a closed three-dimensional oligonucleotide structure comprising y junctions, each junction comprising n double-stranded oligonucleotide arms, wherein: y=8 and n=3, said arms form 12 edges, and every nucleotide residue in said structure is covalently bonded at its 5' and 3' ends to another nucleotide residue, comprising:

hybridizing single-stranded oligonucleotides to form said eight junctions and from zero to eight of said edges, wherein any arms not forming an edge between two junctions have a sticky end complementary to a sticky end of one other of said arms; and forming the remaining edges of said structure by ligating said arms having complementary sticky ends.

9. The method of claim 8 wherein the junctions are at least four immobile oligonucleotide junctions.

10. The method of claim 8 wherein the junctions are eight immobile oligonucleotide junctions.

11. A method for preparing a closed three-dimensional oligonucleotide structure which is a cube comprising y junctions, each junction comprising n double-stranded oligonucleotide arms, wherein: wherein: y=8 and n=3, said arms form 12 edges, and every nucleotide residue in said structure is covalently bonded at its 5' and 3' ends to another nucleotide residue, comprising:

a) preparing first and second oligonucleotide quadrilaterals, each of said quadrilaterals comprising four immobile oligonucleotide branched junctions, each of said junctions having three arms, one arm of each junction of said first quadrilateral having a sticky end complementary to a sticky end of a corresponding arm on said second quadrilateral; and b) ligating each arm with its complementary arm to form the structure.

12. The method of claim 11 wherein step b) comprises (i) hybridizing and ligating each of two arms on adjacent corners of said first quadrilateral to its designated complement on adjacent corners of said second quadrilateral to form a 3-connected object comprising three covalently bonded quadrilaterals having complementary arms on opposite sides;

(ii) separating said 3-connected object; and (iii) ligating the complementary arms on opposite sides of said object to form the structure.

13. The method of claim 1 wherein the oligonucleotides are DNA, step a) is performed by preparing first and second DNA quadrilaterals by the steps of:

(i) self-ligating a first strand to form a first cyclic molecule and self-ligating a sixth strand to form a second cyclic molecule;

(ii) hybridizing and ligating second, third, fourth and fifth strands to said first cyclic molecule and hybridizing seventh, eighth, ninth and tenth strands to said second cyclic molecule to form the first and second quadrilaterals, each quadrilateral having four immobile branched junctions, each junction having three arms, each of said arms having a sticky end complementary to a corresponding sticky end of an arm of the other quadrilateral; and step b) comprises:

(iii) hybridizing and ligating said quadrilaterals together to form a 3-connected object comprising three covalently bonded quadrilaterals having two arms bearing sticky ends at each of the opposite ends of the object;

(iv) subjecting the product of step (iii) to denaturing electrophoresis to obtain a band which contains a linear tricyclic topologically bonded core of the object;

(v) combining the core with the second, third, fourth, seventh, ninth and tenth strands to reform the object; and (vi) hybridizing and ligating the sticky ends on opposite ends of the object to form the structure.

14. A method for preparing a closed three-dimensional oligonucleotide structure comprising y immobile oligonucleotide branched junctions, each junction comprising n double-stranded oligonucleotide arms, wherein: y=8 and n=3, said arms form 12 edges, and every nucleotide residue in said structure is covalently bonded at its 5' and 3' ends to another nucleotide residue, comprising hybridizing single-stranded oligonucleotides to form said eight junctions and from zero to eight of said edges, wherein any arms not forming an edge between two junctions have a sticky end complementary to a sticky end of one other of said arms; and forming the remaining edges of said structure by ligating said arms having complementary sticky ends, wherein each of said junctions is connected via its arms to three other of said junctions.

* * * * *